United States Patent [19]

Hawe et al.

[11] Patent Number: 4,892,916

[45] Date of Patent: * Jan. 9, 1990

[54] POLYMERIC THICKENERS AND THEIR PRODUCTION

[75] Inventors: Malcolm Hawe; David Farrar, both of West Yorkshire, England

[73] Assignee: Allied Colloids Limited, England

[*] Notice: The portion of the term of this patent subsequent to Jun. 30, 2004 has been disclaimed.

[21] Appl. No.: 99,629

[22] Filed: Sep. 22, 1987

Related U.S. Application Data

[63] Continuation of Ser. No. 894,343, Aug. 7, 1986, abandoned, which is a continuation-in-part of Ser. No. 766,097, Aug. 15, 1985, Pat. No. 4,702,844, and a continuation-in-part of Ser. No. 766,098, Aug. 15, 1985, abandoned.

[30] Foreign Application Priority Data

| Aug. 15, 1984 | [GB] | United Kingdom | 8420693 |
|---|---|---|---|
| Aug. 15, 1984 | [GB] | United Kingdom | 8420694 |
| Aug. 15, 1984 | [GB] | United Kingdom | 8420695 |
| Jan. 30, 1985 | [GB] | United Kingdom | 8502329 |
| Aug. 12, 1985 | [GB] | United Kingdom | 8520218 |
| Feb. 14, 1986 | [GB] | United Kingdom | 8603653 |
| Feb. 14, 1986 | [GB] | United Kingdom | 8603652 |
| Feb. 14, 1986 | [GB] | United Kingdom | 8603651 |

[51] Int. Cl.$^4$ ................... C08L 33/14; C08F 265/04
[52] U.S. Cl. .................... 526/304; 526/320; 526/332; 526/333
[58] Field of Search ............ 524/543, 555, 558; 526/304, 320, 332, 333

[56] References Cited

U.S. PATENT DOCUMENTS

| 3,652,497 | 4/1972 | Junas et al. | 525/328.8 |
|---|---|---|---|
| 3,657,175 | 7/1972 | Zimmerman | 524/96 |
| 4,138,381 | 10/1979 | Chang et al. | 524/765 |
| 4,338,239 | 7/1982 | Dammann | 524/549 |
| 4,384,096 | 8/1983 | Sonnabend | 526/313 |
| 4,500,693 | 2/1985 | Takehara et al. | 526/240 |
| 4,677,152 | 6/1987 | Allen et al. | 524/543 |

FOREIGN PATENT DOCUMENTS

| 0013836 | 8/1980 | European Pat. Off. . |
|---|---|---|
| 0048094 | 3/1982 | European Pat. Off. . |
| 0063018 | 10/1982 | European Pat. Off. . |
| 0109820 | 5/1984 | European Pat. Off. . |
| 1167524 | 3/1967 | United Kingdom . |
| 1273552 | 11/1969 | United Kingdom . |

OTHER PUBLICATIONS

Kirk Othmer, Encyclopedia of Polymer Science & Technology, Vol. 1, p. 757.

Yocum & Nyquist, Functional Monomers, vol. 1, pp. 384–387.

*Primary Examiner*—Paul R. Michl
*Assistant Examiner*—Lee C. Wright
*Attorney, Agent, or Firm*—Andrus, Sceales, Starke & Sawall

[57] ABSTRACT

Polymers are made by polymerization of an ionic monomer such as methacrylic acid or dialkylaminoalkyl (meth)-acrylate or -acrylamide and/or a substantially non-ionic monomer, optionally a cross linking agent, and an allyl ether of the formula $CH_2=CR'CH_2OA_mB_nA_pR$ where R' is hydrogen or methyl, A is propyleneoxy or butyleneoxy, B is ethyleneoxy, n is zero or an integer, m and p are zero or an integer less than n, and R is a hydrophobic group of at least 8 carbon atoms. The polymers are preferably made by oil in water emulsion polymerization. They can be used as thickeners particularly in environments containing surfactant and/or electrolyte, including especially emulsion paints, print pastes, alkaline liquors and acidic liquors.

37 Claims, No Drawings

POLYMERIC THICKENERS AND THEIR PRODUCTION

This application is a continuation of copending application Ser. No. 894,343 filed Aug. 7, 1986, now abandoned, which is a continuation-in-part of U.S. Ser. Nos. 766,097, now U.S. Pat. Nos. 4,702,844, and 766,098 now abandoned 15th Aug. 1985.

It is known that aqueous media can be thickened by the presence of high molecular weight synthetic polymers either in solution or in the form of swollen particles. If the polymers are in solution the thickening is probably due to entanglement of polymeric chains. If the polymers are swollen the thickening is probably due to inter-particulate attraction and solvent immobilization.

It is known that thickening in some instances can be improved by including in the polymer pendant hydrophobic groups, the improvement apparently being due to association between the hydrophobic groups in adjacent molecules and the polymers containing such groups are often referred to as associative thickeners.

GB No. 1,167,524 describes thickeners that are said to be effective in solutions of surface active agents and that are copolymers of at least one ethylenically unsaturated monomer with a comonomer that is, for instance, an acrylic ester or an allyl ether of a polyalkoxylated alcohol that may be aliphatic or aromatic. This polyalkoxylated alcohol thus provides the pendant hydrophobic groups. Particular allyl ethers of this general type, and copolymers formed from them, are also described in GB No. 1,273,552.

All the examples in these patents of copolymers using allyl ether show the copolymer to be soluble in water. The comonomer with the ether or ester is said to be acrylic acid, acrylamide, vinyl pyrollidone or maleic anhydride or a blend of maleic anhydride with a compound which normally copolymerises in alternating sequence. The use of maleic anhydride alone or in such a blend will tend to give a low molecular weight compared to the values currently available when copolymerising, for instance, acrylic acid.

In most of the examples the comonomer is maleic anhydride, optionally with methyl vinyl ether, but in example 12 of GB No. 1,167,524 and example 8 of GB No. 1,273,552 the allyl ether is copolymerised with acrylic acid to form a water soluble polymer. The information in each example suggests that the molecular weight is low.

In all of the examples showing the use of allyl ethers, polymerization is conducted by precipitation polymerization. Thus polymerization is conducted in a liquid that is a solvent for the monomer but not for the polymer, so that polymer is precipitated out of the solution during polymerization. This technique tends to produce rather low molecular weights.

The intention to form low molecular weight compounds is emphasized by example 13 of GB No. 1,167,524 in which a copolymer is formed by aqueous solution polymerization of acrylamide and an acrylic ester with a polyethoxylated nonyl phenyl alcohol since isopropanol is included in the polymerization mixture. This will ensure that a relatively low molecular weight polymer is produced.

It is well known that allyl monomers po.ymerise much less readily, and yield copolymers of lower molecular weights, than acrylic or other vinyl monomers. In U.S. Pat. No. 4451628 allyl sulphonate is used to depress molecular weight. Another allyl monomer is diallyl dimethyl ammonium chloride and it is well known that polymers of this generally have a maximum molecular weight of below 500,000.

The fact that the use of allyl monomers causes the resultant homo- or co-polymer to be of low molecular weight is discussed frequently in the literature, for instance in "Functional Monomers" Volume 1 edited by Yocum and Nyquist pages 384 to 387. It is stated in this that allyl monomers po.ymerise with difficulty to give products of low molecular weight and their presence will retard both the rate and degree of polymerization of other copolymerisable monomers. It is stated that the polymerization kinetics of allyl monomers are determined by degradative chain transfer which results in the formation of a stable radical that has low activity for chain propogation. The article describes ways of trying to obtain higher molecular weights but the highest value obtainable is said to have a degree of polymerization of the order of 1,000 to 10,000. The molecular weight is therefore still low by the standards of acrylic or other vinyl monomers since these can easily be po.ymerised to molecular weights in the range 10 million to 30 million, provided chain transfer agent is omitted.

Since the techniques and comonomers that were specifically described in GB No. 1,167,524 were all such as to lead inevitably to relatively low molecular weight polymers it was reasonable to propose the use of allyl ether monomers. They would be expected to give the sort of molecular weights that clearly were intended to be achieved in the processes of that patent and GB No. 1,273,552. In practice the products of these patents have not proved commercially very successful.

In marked contrast to these low molecular weight allyl ether and acrylate copolymers has been the commercial success of associative polymers formed solely from acrylic monomers and by techniques that would normally be expected to give high molecular weights. The literature relating to these polymers generally indicates molecular weights in the range 100,000 (in the presence of chain transfer agent) to several million. Instead of making the polymers in the presence of a relatively large amount of isopropanol or by precipitation polymerization or using comonomers such as maleic anhydride blends, all of which will tend to give low molecular weights, the successful associative thickeners are generally made by oil-in-water emulsion polymerization or by aqueous solution or gel polymerization, and can have very high molecular weights. If for a particular purpose the highest molecular weights are to be avoided very low amounts of chain transfer agent are incorporated to depress molecular weight but the resultant molecular weights will generally still be well above those made by the processes described in GB No. 1167524 and 1273552.

In EP No. 48094 the pendant hydrophobic group is introduced as a polymerization initiator or chain transfer agent (tending to depress molecular weight) in the polymerization of acrylamide. In EP No. 63018 and U.S. Pat. Nos. 4,423,199 and 4,524,175 the hydrophobic group is introduced as a substituent in acrylamide.

The JP No. 60-235815A the pendant hydrophobic group is introduced as a vinyl ether.

The great majority of literature on associative thickeners, and all commercial products, introduces the hydrophobic group as an ester of an unsaturated carboxylic acid (generally (meth) acrylic acid) that is copolymerised with one or more monomers that are always vinylic, and are usually (meth) acrylic. Thus in U.S. Pat. Nos. 3,915,921 and 4,190,562 the hydrophobic group is introduced as a $C_{10-30}$ alkyl ester of (meth) acrylic acid. In U.S. Pat. Nos. 4,138,381, 4,268,641, 4,384,096 and 4,463,151, EP No. 13836 and EP No. 109820 and in GB No. 1,167,524 an ester is formed between an unsaturated acid and a hydrocarbyl ether of a polyalkylene glycol.

When the polymers are linear it is clear that increasing molecular weight generally gives increasing thickening properties (although it may also give flocculation of suspended solids) and so the use of monomers that make it impossible to obtain high molecular weights is clearly contra-indicated. In those particular instances where lower molecular weight is desired, e.g., if flocculation of suspended solids is to be avoided, then this is best achieved commercially by using the same monomer blend as will give high molecular weight together with a low amount of a chain transfer agent such as a mercaptan.

Similarly, when the polymers are cross linked experience in other polymerization techniques for making thickeners generally indicates that the best polymer properties are obtained when the cross linked polymer is formed from monomers that, in the absence of cross linking agent, would give the highest possible molecular weight. Thus cross linked polymers should also be formed from acrylic monomers in the absence of monomers that will significantly reduce molecular weight.

The present state of the art therefore is that when manufacturing cross linked or, especially, linear polymers that are to be used for, for instance, thickening the best properties generally follow from the use of monomers capable of polymerizing to very high molecular weights optionally with a chain transfer agent such as a mercaptan, allyl monomers are known to be incapable of giving high molecular weights, and the processes in GB Nos. 1,167,524 and 1,273,552 clearly all gave linear polymers of molecular weights much less than those that would now be considered to be necessary for satisfactory properties.

Polymers such as those described in EP No. 13836 are made by oil-in-water emulsion polymerization and swell or dissolve upon the addition of alkali. They have proved commercially successful but there is still considerable room for improvement in their properties.

For instance one use of the polymers is for thickening aqueous solutions containing an electrolyte. The solutions may therefore have relatively high pH. Also they may be used under conditions of high temperature. Unfortunately high pH and/or high temperature can result in hydrolysis of the ester linkage by which the hydrophobic group is attached.

A problem that is often encountered commercially with thickeners such as in EP No. 13836 is that they may cause foaming, and print quality (when used in textile printing pastes) may need improvement in some instances.

Despite all the experience indicating that it is essential to use, when making thickeners, only monomers capable of giving high molecular weight polymers, we have now found that a particular class of new polymers formed from monomers including a particular type of allyl monomer have surprisingly valuable thickening properties.

A polymer according to the invention is selected from linear polymers having intrinsic viscosity (as herein defined) above 0.5 dl/g, cross linked polymers and polymers that are insoluble and non swellable in water but that are soluble or swellable in aqueous acid or aqueous alkali and which are formed by polymerization of (a) 0 to 90% of ethylenically unsaturated ionic monomer, (b) 0 to 90% of ethylenically unsaturated substantially non-ionic monomer, (c) 0.5 to 100% of ether of the formula $CH_2=CR'CH_2OA_mB_nA_pR$ where R' is hydrogen or methyl, A is propyleneoxy or butyleneoxy, B is ethyleneoxy, n is zero or an integer, generally 1 to 100, m and p are each zero or an integer less than n and R is a hydrophobic group of at least 8 carbon atoms, (d) 0 to 5% of cross linking agent, preferably a copolymerisable polyethylenically unsaturated monomer.

Throughout this specification all percentages are by weight unless otherwise specified. All intrinsic viscosities are single point intrinsic viscosity as measured at 0.05% polymer concentration in methanol.

The preferred polymers of the invention are made by oil-in-water emulsion polymerization and are substantially insoluble and non swellable in water but are soluble or swellable in aqueous acid or aqueous alkali and are formed from 5 to 90% of monomer (a), 5 to 90% of monomer (b), 0.5 to 90% of monomer (c) and 0 to 5% of monomer (d), and so the invention is now described with particular reference to these.

The oil-in-water emulsion polymerization is conducted using sufficient of an appropriate emulsifier, as is conventional. The final polymer is insoluble and substantially unswollen in the aqueous phase of the polymerization mixture but, due to the ionic monomer, is soluble or swellable upon appropriate pH adjustment, generally to below pH 7 when the monomer (a) is free amine and to above pH 7 when the monomer (a) is free acid. The solubility of the monomers in the aqueous phase may be conventional for oil-in-water emulsion polymerization. Generally the blend of monomers, and often each monomer, is insoluble in the aqueous phase but some water solubility can be tolerated provided the monomers all migrate during the polymerization into the micelles of emulsifier.

Monomer (a) is preferably a vinyl, generally acrylic, monomer and may be a co-ionic blend of monomers. When monomer (a) is anionic upon addition of alkali, the monomer and its amount must be such that addition of alkali renders the polymer soluble or swellable. The monomer is generally a carboxylic monomer as free acid during the polymerization. The monomer generally contains 3 to 8 carbon atoms. It may be a monocarboxylic acid, a dicarboxylic acid or, for instance, a monoalkyl ester of a dicarboxylic acid. The acid may be selected from acrylic, methacrylic, itaconic, crotonic, fumaric, citraconic acryloxypropionic or maleic acids. Preferably at least 50%, and most preferably 100%, of component (a) is provided by methacrylic and/or acrylic acid, with methacrylic being particularly preferred.

When monomer (a) is cationic, the monomer and its amount must be such that the addition of acid or quaternising compound, renders the polymer soluble or swellable. The monomer generally includes a tertiary amine group as a free base during polymerization and this is then converted to the cationic form as an acid salt or quaternary ammonium salt. Dialkylaminoalkyl (meth) acrylamides may be used. For instance the aminoalkyl group may contain 2-8 carbon atoms, preferably 1,3-propylene, and the other alkyl groups may contain 1 to 4 carbons. The preferred monomers are dialkylaminoalkyl (meth) acrylates. The preferred monomers are dimethylaminoethyl (meth) acrylates and dimethylaminopropyl (meth) acrylamides.

The amount of monomer (a) must be such that the blend of components (a), (b), (c) and (d) can be po.ymerised by oil-in-water emulsion polymerization to form an emulsion of the polymeric thickener in which the polymer is insoluble and substantially unswollen and non-thickening but that, after polymerization, the emulsion can be converted by addition of alkali or acid into a viscous system thickened by the polymer. It is generally necessary for there to be at least 10%, usually at least 20% and preferably at least 30% of the ionic monomer. The amount is generally below 70%, usually below 60%.

Monomer (b) is preferably a vinyl, generally acrylic, monomer and may be a blend of monomers. The monomers are generally water insoluble but a minor proportion of monomer (b) may be a water soluble monomer such as acrylamide. By water insoluble monomer in the context of the present specification we mean monomer that is soluble in water to a degree of up to 5% at room temperature. Suitable monomers are styrene and alkyl and/or halo-substituted styrenes, (meth) acrylonitrile, vinyl alkanoates (especially the acetate), vinyl and vinylidene halides (especially the chloride), hydroxy alkyl and alkoxy alkyl (meth) acrylates and alkyl (meth) acrylates. Preferred monomers are styrene, 2-hydroxy ethyl acrylate, acrylonitrile, vinyl chloride and vinyl acetate and the alkyl (meth) acrylates. Preferably at least 50% by weight of component (c), and most preferably 100%, is alkyl (meth) acrylate. In all these monomers any alkyl groups may contain 1 to 8 carbon atoms but particularly preferred monomers are C1-4 alkyl (meth) acrylates such as methyl methacrylate, butyl acrylate or, ethyl acrylate.

Monomer (b) is generally present in an amount of at least 15%, usually at least 20% and preferably at least 30%. The amount is generally below 80%, usually below 70% and preferably below 60%.

Normally monomers (a) and (b) are free of hydrophobic groups R and should preferably be conventional low molecular weight monomers.

Monomer (c), which is referred to below as the "allyl ether", preferably includes a polyethoxy chain and so n is generally above 2, often above 5 and frequently above 10 or 15 up to 50 or even up to 100. m and p are each generally zero. Thus a polyoxyethylene chain between the allyl group and the hydrophobe is generally present but it may be interrupted by oxypropylene and/or oxybutylene groups. By appropriate choice of the values of n, m, p and R it is possible to control the solubility of the monomer and the properties of the final polymer. R' is generally hydrogen.

R is a hydrophobic group containing at least 8 carbon atoms. It can be a polyoxyalkylene chain where the alkylene groups wholly or mainly are propylene or butylene or higher but preferably is a hydrocarbyl group.

The hydrocarbyl group generally contains from 8 to 30, preferably 10 to 24 and most preferably 12 to 18 carbon atoms. It may be selected from alkyl, for instance octyl, lauryl or stearyl, aralkyl such as 2-phenyl ethyl (—$C_2H_4Ph$), aryl such as naphthyl, alkaryl such as alkyl phenyl wherein the alkyl group generally contains 6 to 12 carbon atoms, cycloalkyl (including polycyclic alkyl groups), or mixtures of one or more such groups. Preferred hydrocarbyl groups are alkyl and alkaryl groups. Any of these groups may additionally be substituted provided the substituents do not render the pendant group hydrophilic to an extent that the desired improvement in properties due to the hydrophobic group is lost.

The amount of the allyl ether is generally at least 1% and usually at least 2%. It is generally below 70% and usually below 50%. Amounts in the range 5 to 30% are often preferred.

The allyl ethers may be made by methods such as those described in GB No. 1,273,552, for instance by reacting an appropriate surfactant alcohol with sodium or sodium alkoxide, generally in the absence of water but in a solvent such as xylene, to form the sodium derivative and then reacting this with allyl chloride, or by reacting allyl alcohol with the surfactant alcohol with or without catalyst. Preferably however the allyl ethers are made by the method described in our copending application filed even date reference and entitled "Monomer Preduction" Ser. No. 894,352.

Monomer (d) is optional and serves as a cross linker. Suitable cross linkers for emulsion po.ymerised ethylenically unsaturated monomers are well known. They are generally polyethylenically unsaturated monomers materials such as diallyl phthalate, allyl (meth) acrylate, divinyl benzene, (poly)ethylene glycol dimethacrylate and methylene bis acrylamide. If the cross linker is present its amount is generally in the range 0.0005 to 5% (5 to 50,000 ppm), generally below 1%, most preferably 0.001 to 0.2%.

Particularly preferred copolymers are those formed from 20 to 60% by weight acrylic acid and/or methacrylic acid (preferably methacrylic acid alone), 5 to 60% ethyl acrylate or other suitable alkyl (meth) acrylate and 2 to 50% of the allyl ether, optionally with cross linker.

Other preferred polymers are formed from 20 to 60% dialkylaminoalkyl (meth) -acrylate or -acrylamide, 5 to 60% ethyl acrylate or methyl methacrylate or other alkyl (meth) acrylate, with 2 to 50% monomer (c), and optionally (d).

The polymers may have a molecular weight well above 0.5 million and generally above 1 million, e.g. above 2 million and often above 5 million, when they are prepared in the absence of chain transfer agents. This is far in excess of what would be expected from knowledge of allyl polymerizations in general. However for some purposes the highest molecular weights are undesirable because of the risk of flocculation occurring when the thickener is used in a system containing suspended solids. Accordingly it is sometimes desirable to po.ymerise in the presence of a chain transfer agent in order to depress molecular weight, e.g. down to 10,000 or 200,000.

The intrinsic viscosity (namely the single point intrinsic viscosity as measured at 0.05% polymer concentration in methanol) of linear polymers is generally at least 0.5 and when there is no solid phase the IV is preferably at least 1 and preferably at least 2, 3 or even 5, for instance it may be 5-10 or higher.

Cross linked, emulsion po.ymerised, polymers are polymers made from monomers (a), (b) and (c) under conditions that would, in the absence of cross linker (d), lead to linear polymers having these preferred molecular weight and viscosity properties.

The emulsion po.ymerised polymers of the invention differ from those of GB No. 1,167,524 and 1,273,552 in a number of respects. They are made by oil-in-water emulsion polymerization, this permitting much higher molecular weights. They are insoluble and unswollen at the pH at which they are manufactured, and soluble or swollen at another, whereas the anionic polymers of GB No. 1,167,524 are water soluble. The molecular weights that are obtained in the invention can be very much higher than anything obtainable in those patents. The reason for our being able to obtain high molecular weights is not clear but may be due to the effect of the group —$A_mB_nA_pR$ on the polymerization properties of the allyl monomer. The comonomers preferably are such as to permit high molecular weights and preferably are not such as to reduce molecular weight (e.g., maleic anhydride with methyl vinyl ether, as in those patents).

Other disclosures of polymers containing allyl ethers are in EP No. 0172723, 0172724 and 0172025, none of which were published at the priority date of this application and all of which, so far as the allyl ether disclosure is concerned, have the same priority date as this application.

The polymers differ from the polymers disclosed in, for instance, EP No. 13836 by omitting the acrylic ester for introducing the hydrophobic group and using instead the defined allyl ether. It is very surprising that this substitution can be made without seriously reducing the molecular weight and without damaging the properties of the polymer. It is surprising that the polymers have viscosity and other properties at least as good as those of EP No. 13836 and in many respects better. By the invention the risk of the hydrophobic group being hydrolysed out of the polymer chain by thermal or pH hydrolysis of the ester linkage is eliminated. It is also possible to avoid the other problems outlined above.

The oil-in-water emulsion polymerization may be conducted in conventional manner, for instance as described in EP No. 13836. Emulsifier is included to maintain the monomer and the polymer in stable dispersed condition and to provide micelles for the polymerization. When monomer (a) is anionic, suitable emulsifiers are anionic, such as sodium alkyl phenyl ether sulphate or sodium lauryl sulphate or sodium dodecyl benzene sulphonate, but may be non ionic. When monomer (a) is cationic, the emulsifier is preferably non-ionic.

The initiator is preferably a water soluble initiator, most preferably an alkali metal or ammonium persulphate, generally in an amount up to 1% based on the monomers. Preferably polymerization is started and further monomer is then added. The polymerization temperature is generally in the range 60° to 100° C.

Although it is generally undesirable, in some instances a chain transfer agent such as an alkyl mercaptan may be added to the monomer in order to depress molecular weight for example to minimize flocculation during thickening.

The amount of monomer, and thus of polymer, in the emulsion is generally from 20 to 60%, most preferably 25 to 50%, based on the weight of emulsion. The emulsion has a pH at which the polymer is insoluble and substantially unswollen in water (7 or below when monomer (a) is anionic and 7 or above when it is cationic) but upon addition of alkali or acid (for anionic or cationic polymers respectively) the polymer dissolves or swells and will form a very viscous composition. The polymer can be isolated from the water after or, preferably, before the adjustment of pH by, for instance, spray or drum drying to form a powder or the polymer may be converted to a concentrated, substantially anhydrous, dispersion in a non-aqueous liquid as described in EP No. 0172025. Often however it is convenient to use the polymer in the form of the oil-in-water emulsion in which it is initially produced. The pH adjustment may be made to this emulsion before use but preferably the emulsion is added to the phase that is to be thickened while the polymer is still insoluble and unswollen and the polymer is converted to a viscous thickener by reaction with alkali or acid in the aqueous phase. The pH of this aqueous phase may be as high as, for instance, 13 or 14 when the monomer (a) is anionic and as low as 1 or 2 when monomer (a) is cationic.

The emulsion po.ymerised polymer is generally supplied to the user as an oil-in-water emulsion but if desired may be converted to a water-in-oil dispersion (or a dehydrated product thereof) before use, e.g., as described in EP No. 172025.

Improved thickening is often achieved in the presence of a surface active agent, generally in an amount of from 0.05 of 1 part by weight surfactant per part by weight polymer. Surfactants that will give this effect may be selected from anionic, non-ionic, amphoteric or cationic provided they are compatible with the polymer and the other components of the aqueous phase. Preferably they are non-ionic or anionic. Preferred surfactants are ethoxylated linear alkyl ethers or ethoxylated alkyl phenyl ethers. Often the surfactant is the same as or similar to a surfactant alcohol that has been used to form the allyl ether.

The polymers are of particular value for thickening aqueous media containing electrolyte and optionally containing a dispersed phase. For instance the polymers may be used for thickening chemically toxic aqueous compositions. These may be alkaline compositions such as bleaches, caustics and paint removers when monomer (a) is anionic. They may be acidic when monomer (a) is cationic. For instance a cationic polymer may be introduced into an environment and then thickened by adding acid.

The polymers (especially when monomer (a) is anionic) are of particular value for thickening aqueous latex paints, both matt, semi-matt and gloss paints. These may contain conventional pigments, dispersants and binders.

The polymers (especially when monomer (a) is anionic) are also of great value for thickening textile print pastes. Such systems include for example reactive dye or acid dye, or pigment pastes especially where such pastes are prone to gelling. The other components of the print paste may be conventional. In such pastes they not only have the valuable high shear and low shear viscosity properties that are useful in all thickening situations but they also have the advantage of minimising flushing of the print color. Particularly good results are obtained in combination with surfactant.

Other uses for the polymers are for thickening oils, as water retention aids, e.g. in cements, and as deicing fluids, for thickening brine (e.g., downhole), for thickening carpet backing latices and for thickening textile sizing solution.

The amount of polymer used is generally in the range 0.05 to 5% weight based on the water content of the aqueous phase that is to be thickened.

The polymers can be used for other purposes, e.g., as wallpaper adhesives.

The invention also includes water insoluble, acid or alkali swellable or soluble, polymers made by other techniques, e.g., polymerization in solution in organic solvent.

The invention also includes linear polymers irrespective of how they are made and having IV of at least 0.5. They may be water insoluble and made from the monomer blends and by the methods described above or they may be water soluble. For instance they may be made from 0.5 to 100% monomer (c) and 0–99.5% water soluble monomers (a) and (b). These may have IV 0.5 to 1 or higher, e.g., as described above.

Monomer (c) may be as described above. The polymers are preferably non ionic or anionic.

The preferred soluble polymers have, as monomers (a) and (b), water soluble anionic monomer optionally blended with acrylamide, water soluble cationic monomer optionally blended with acrylamide, or acrylamide. Naturally the monomers should be free of pendant hydrophobic groups. 0–20%, generally 0–10% and preferably 0%, water insoluble monomer (b) can be included.

One class of preferred soluble anionic copolymers of the invention are formed of 5 to 50%, preferably 20 to 40% acrylic acid or other unsaturated carboxylic or sulphonic acid, generally as a sodium or other salt thereof, 50 to 90%, preferably 60 to 80%, by weight acrylamide and 2 to 30% by weight of the allyl ether.

Another class of preferred soluble anionic copolymers are formed of 50 to 100% (often 80–100%) of the acid, 0 to 50% (often 0–20%) acrylamide and 2 to 30% of the allyl ether.

Preferred cationic soluble polymers of the invention are formed of 10 to 99% and preferably 20 to 70% dialkyl amino alkyl (meth)-acrylate or -acrylamide quaternary or free acid salt, 0 to 80% preferably 20 to 70% acrylamide, and 1 to 90%, preferably 5 to 50%, of the allyl ether.

The water soluble polymers can be made by conventional methods of making water soluble polymers but modified by the incorporation of the allyl ether, e.g., as in EP No. 0172723. Thus they may be made by aqueous gel polymerization or by reverse phase polymerization. This process may be conducted to a very small dry particle size, such as below 4 μm, for instance as described in European application No. 0172724 or may be conducted as a bead polymerization process, using conventional water soluble initiators, stabilizers and, if desired, emulsifiers. Suitable materials are described in that application. Linear water-soluble products may be made as in either of these specifications in the absence of cross-linking monomer.

The soluble polymers may be provided as dispersions in non-aqueous liquid or as dry particles, for instance made by bead polymerization followed by drying and filtering or made by gel polymerization followed by drying and comminuting. Depending upon the solubility of the monomers used for their manufacture the polymers will either be truly water soluble or will be water swellable.

These polymers are useful as flocculants, for instance as described in EP No. 017273. In addition to acting as flocculants for, for instance, sewage or inorganic dispersions they are also of value as filtration aids and paper retention aids, as gangue suppressants as clarification improvers, for pelletising minerals, as dewatering aids or filtration rate improvers as drift controllers in agricultural spray compositions, as soil stabilizers or dust suppressants, and, especially, as thickeners for aqueous liquids.

They are particularly effective for thickening any of the compositions described above including paints, textile print pastes, or chemically toxic and other aqueous compositions such as bleaches, caustics and paint remover compositions and, especially, for thickening brine, drilling muds and other downhole electrolyte liquors such as for acidising or fracturing, especially when the polymer contains sulphonate groups or cationic groups. Other downhole uses are as viscosifiers for enhanced oil recovery, drilling fluids or shut off fluids, as fluid loss additives, and for polymer flooding. They may be used with surfactant, as described above. The soluble linear polymers may have better suspending properties in respect of large or heavy inorganic particles than the emulsion polymers discussed above.

Another use for the water soluble polymers is as an aqueous adhesive, for instance a wallpaper adhesive that may be a brush-on composition or a prepaste.

The invention also includes cross linked polymers. They may be non swellable in water but swellable in acid or alkali and so may be made by emulsion or organic solution polymerization as described above. They may be formed of 0.5 to 100% monomer (c) and 0–99.5% monomers (a) and (b), and 0.0001 to 5% cross linking agent, where all the monomers may be as discussed above for emulsion po.ymerised polymers.

Preferably the cross linked polymers are water swellable and the monomers and the polymerization conditions, are preferably such that in the absence of the cross linking monomer the polymer would have IV at least 1, generally at least 2 and preferably at least 3, often above 5, for instance 10 to 20.

Preferred water swellable polymers are formed from 1 to 100% of the allyl ether, 0 to 99% water soluble monoethylenically unsaturated monomer and 0 to 20%, generally 0 to 10% and preferably 0% of water insoluble monoethylenically unsaturated monomer. Suitable water soluble monomers are discussed above.

Preferred swellable polymers have, as monomer (b), water soluble anionic monomer optionally blended with acrylamide, water soluble cationic monomer optionally blended with acrylamide, or acrylamide. Naturally the monomers (b) should be free of pendant hydrophobic groups.

One class of preferred swellable anionic copolymers are formed of 5 to 50%, preferably 20 to 40% acrylic acid or other unsaturated carboxylic or sulphonic acid, generally as a sodium or other salt thereof, 50 to 90%, preferably 60 to 80%, by weight acrylamide and 2 to 30% by weight of the allyl ether, and cross linking agent.

Another class of preferred anionic copolymers are formed of 50 to 100% (often 80–100%) of the acid, 0 to 50% (often 0–20%) acrylamide and 2 to 30% of the allyl ether, and cross linking agent.

Preferred cationic polymers of the invention are formed of 10 to 99% and preferably 20 to 70% dialkyl amino alkyl (meth)-acrylate or -acrylamide quaternary or free acid salt, 0 to 80% preferably 20 to 70% acrylamide, and 1 to 90%, preferably 5 to 50%, of the allyl ether, and cross linking agent.

The water swellable polymers can be made by conventional methods of making water swellable polymers but modified by the incorporation of the allyl ether. Thus they may be made by aqueous gel polymerization or by reverse phase polymerization. This process may be conducted to a very small dry particle size, such as below 4 μm, for instance as described in European application No. 0172724 or may be conducted as a bead polymerization process, using conventional water soluble initiators, stabilizers and, if desired, emulsifiers. Suitable materials are described in that application.

The polymers may be provided as dispersions in non-aqueous liquid or as dry particles, for instance made by bead polymerization followed by drying and filtering or made by gel polymerization followed by drying and comminuting.

When the polymerization is conducted to give a small particle size, for instance below 4 microns dry size, and especially when the comonomers are anionic, especially acrylic acid (for instance as ammonium or sodium acrylate) alone or blended with acrylamide the resultant compositions are particularly useful as textile print paste thickeners.

Anionic water swellable polymers having a particle size of, for instance, 50 to 500 μm dry size are particularly valuable as absorbents, for instance in diapers or for dewatering slurries or conditioning soil. Suitable polymers for this purpose are generally formed of 2 to 50% (preferably 3 to 30%) of the allyl ether, 0 to 70% (preferably 30 to 60%) acrylamide and 20 to 98%, preferably 30 to 50%, sodium acrylate and 0.001 to 0.1% cross linking agent. The polymers may be made by gel polymerization, drying and comminution to the desired size or by reverse phase bead polymerization.

Alkali swellable, small particle size, polymers from water insoluble monomers are particularly effective for thickening latex paints and chemically toxic and other aqueous compositions such as bleaches, caustics and paint remover compositions and, especially, for thickening brine, drilling muds and other downhole electrolyte liquors such as for acidising or fracturing especially when the polymer contains cationic groups or sulphonate groups. Other downhole uses include viscosifiers for enhanced oil recovery, drilling fluids or shut off fluids, as fluid loss additives, and for polymer flooding.

Other uses for the water swellable polymers is as an aqueous adhesive, for instance a wallpaper adhesive that may be a brush-on composition or a prepaste, as deicing fluids, or as water retention aids.

When the polymer is present as water swellable beads the surface of the particles is preferably less swellable than the inner parts of the particles, preferably as a result of cross linking the surface layer in known manner (e.g., U.S. Pat. Nos. 3,114,651, 4,043,952 or 4,090,013. This treatment can reduce the stickiness of the particles and can improve the absorption properties.

The following are some examples.

EXAMPLE 1

An emulsion of momomers in water was prepared by mixing 100 g of ethyl acrylate, 80 g of methacrylic acid, 20 g of allyl ether of 10 mole ethoxylate of stearyl alcohol, 5 g of Perlankrol ESD (trade mark), 0.3 g ammonium persulphate and 200 g water. To a reaction vessel containing 2.5 g Perlankrol ESD, 0.1 g ammonium persulphate in 255.8 g water at 85° C., degassed for 30 minutes with nitrogen there was added 5% of the monomer emulsion over a period of 10 minutes.

After the initial charge had po.ymerised at 85° C., the remaining monomer emulsion was gradually added over a period of two hours at 85° C. After completion of the monomer feed, the mixture was held at 85° C. for 15 minutes and then 10 g of 1% ammonium persulphate solution was added. After another 45 minutes, the mixture was cooled and filtered.

The filtrate was approximately 30% solids emulsion copolymer in which the polymer composition is 10% of the allyl ether, 50% ethyl acrylate and 40% methacrylic acid.

The polymer thus prepared was designated Product A. Further samples of varying composition were prepared using this procedure. These were designated in turn as Products B-U. Solutions in water were prepared by neutralization with ammonia to pH 7 or above and the resulting viscosity was measured using a Brookfield RVT viscometer. This data along with composition variables is given in Tables 1a, 1b, and 1c.

Note In table 1
MAA=methacrylic acid
EA=ethyl acrylate
AES=allyl ether surfactant of formula

where
R'=H
B=(CH$_2$—CH$_2$—O)
and n and R are as stated.

In table 1a POLYMER H was prepared without using an allyl ether surfactant monomer. This therefore served as a control.

TABLE 1a

| PRODUCT | MONOMER RATIOS (% by wt) | | | SURFACTANT COMPOSITIONS | | SOLUTION VISCOSITY |
|---|---|---|---|---|---|---|
| | MAA | EA | AES | n | R | (cp)10 rpm |
| POLYMER A | 40 | 50 | 10 | 10 | Stearyl | 14000 |
| POLYMER B | 40 | 50 | 10 | 2 | Stearyl | 8400 |
| POLYMER C | 40 | 50 | 10 | 20 | Stearyl | 7200 |
| POLYMER D | 40 | 50 | 10 | 4 | Lauryl | 150 |
| POLYMER E | 40 | 50 | 10 | 23 | Lauryl | 600 |
| POLYMER F | 40 | 50 | 10 | 30 | C$_{22}$ | 140000 |
| POLYMER G | 40 | 50 | 10 | 25 | Octylphenyl | 500 |
| POLYMER H | 40 | 60 | — | — | — | 60 |

Note:
n-dodecyl mercaptan was included in each of the above recipes, at 0.2% on total monomer.

TABLE 1b

| PRODUCT | MONOMER RATIOS (% by wt) | | | SURFACTANT COMPOSITIONS | | SOLUTION VISCOSITY |
|---|---|---|---|---|---|---|
| | MAA | EA | AES | n | R | (cp)10 rpm |
| POLYMER J | 40 | 55.0 | 5.0 | 10 | Stearyl | 1280 |

TABLE 1b-continued

| PRODUCT | MONOMER RATIOS (% by wt) | | | SURFACTANT COMPOSITIONS | | SOLUTION VISCOSITY (cp)10 rpm |
|---|---|---|---|---|---|---|
| | MAA | EA | AES | n | R | |
| POLYMER K | 40 | 52.5 | 7.5 | 10 | Stearyl | 20800 |
| POLYMER L | 40 | 50.0 | 10.0 | 10 | Stearyl | 26200 |
| POLYMER M | 40 | 47.5 | 12.5 | 10 | Stearyl | 38000 |
| POLYMER N | 40 | 45.0 | 15.0 | 10 | Stearyl | 53600 |
| POLYMER P | 40 | 42.5 | 17.5 | 10 | Stearyl | 72000 |
| POLYMER Q | 40 | 40.0 | 20.0 | 10 | Stearyl | 93200 |

Note:
n-dodecyl mercaptan was included in each of the above recipes at 0.1% on total monomer.

TABLE 1c

| PRODUCT | MONOMER RATIOS (% by wt) | | | SURFACTANT COMPOSITIONS | | SOLUTION VISCOSITY (cp)10 rpm |
|---|---|---|---|---|---|---|
| | MAA | EA | AES | n | R | |
| POLYMER L | 40 | 50 | 10 | 10 | Stearyl | 100000 |
| POLYMER R | 30 | 60 | 10 | 10 | Stearyl | 31000 |
| POLYMER S | 25 | 65 | 10 | 10 | Stearyl | 15800 |
| POLYMER T | 20 | 70 | 10 | 10 | Stearyl | 12200 |
| POLYMER U | 15 | 75 | 10 | 10 | Stearyl | 260 |

Note:
n-dodecyl mercaptan was included in each of the above recipes at 0.1% on total monomer.

EXAMPLE 1d

The effectiveness of polymers AA-AF prepared from other alkyl (meth) acrylate/carboxylic acid monomers is shown.

TABLE 1d

| Product | Monomer Ratio (% by wt.) | | | | | | | | Solution Viscosity (cP) at 10 rpm |
|---|---|---|---|---|---|---|---|---|---|
| | MAA | AA | IA | MA | EA | BA | MMA | AES | |
| Polymer AA | 40 | — | — | 50 | — | — | — | 10 | 76300 |
| Polymer AB | 40 | — | — | — | — | 50 | — | 10 | 2400 |
| Polymer AC | 35 | 5 | — | 50 | — | — | — | 10 | 42400 |
| Polymer AD | 30 | 10 | — | 50 | — | — | — | 10 | 11300 |
| Polymer AE | 37.5 | — | 2.5 | 50 | — | — | — | 10 | 48000 |
| Polymer AF | 40 | — | — | — | 25 | — | 25 | 10 | 2940 |

Note:
n-dodecyl mercaptan was included in each of the above recipes at 0.1% on total monomer.

The abbreviations used to denote the monomer are as follows:
MAA=methacrylic acid
AA=acrylic acid
IA=itaconic acid
MA=methyl acrylate
EA=ethyl acrylate
BA=butyl acrylate
MMA=methyl methacrylate
AES=allyl ether surfactant as previously defined with n=10 and R=stearyl.

EXAMPLE 2

The influence of electrolyte on the thickening efficiency of products of this type was investigated. Three polymers, having compositions as described below were prepared as 2.0% active solutions in deionised water and 0.5% NaCl solution. Solution viscosities were measured using a Brookfield RVT viscometer over a range of speeds as indicated.

POLYMER V: As POLYMER A but without n-dodecyl mercaptan

POLYMER W: As POLYMER v but with 250 ppm diallylphthalate.

POLYMER X: As POLYMER H but with 250 ppm diallylphthalate

TABLE 2

| PRODUCT | 2.5 rpm | | 10 rpm | | 100 rpm | |
|---|---|---|---|---|---|---|
| | $H_2O$ | 0.5% NaCl | $H_2O$ | 0.5 NaCl | $H_2O$ | 0.5% NaCl |
| POLYMER V | 200000 | 272000 | 130000 | 180000 | 28500 | 35000 |
| POLYMER W | 284000 | 240000 | 180000 | 85000 | 25000 | 22000 |
| POLYMER X | 150000 | 11200 | 22000 | 3700 | 4200 | 680 |

Polymer X having no allyl ether surfactant monomer was present to serve as a control.

Polymer V had intrinsic viscosity of 2.5 measured by single point method in methanol at 0.05%.

EXAMPLE 3

The influence of additional surfactant on the thickening efficiency of products of this type was investigated. To 2.0% active solutions of POLYMER A was added increasing amounts of various surfactants. The solution viscosity was remeasured after each addition, and is listed in Table 3 as an index relative to the initial viscosity in the absence of surfactant.

TABLE 3

| SURFACTANT TYPE | SURFACTANT CONCENTRATION | | |
|---|---|---|---|
| | 0.1% | 0.2% | 0.3% |
| Lauryl alcohol.4 ethoxylate | 188 | 258 | 271 |
| Stearyl alcohol.10 ethoxylate | 104 | 115 | 135 |
| Sodium Lauryl sulphate | 163 | 625 | 798 |
| Sodium $C_{12}$–$C_{15}$ alcohol ether sulphate | 149 | 214 | 244 |

EXAMPLE 4

To demonstrate the greater stability attained by linking the hydrophobe through an ether linkage rather than an ester linkage, and to eliminate variables due to other monomers in the polymer, a comparison was conducted between the hydrolytic stability of the ester of acrylic acid with polyoxyethylene (23 moles) lauryl ether and of the ether of the same lauryl ether with allyl alcohol (formed by reacting the sodium derivative of the ether with allyl chloride).

A 2.0% solution of each monomer was placed in a thermostated water bath at 45° C. Each was taken to pH 11.0 with 0.0986 M NaOH. The pH was checked every hour and readjusted to pH 11.0 by the addition of further NaOH. The volume of NaOH required was noted and hence the percentage hydrolysis was calculated for each monomer.

TABLE 4

| TIME | ACRYLATE MONOMER | | ALLYL ETHER MONOMER | |
|---|---|---|---|---|
| hours | Vol NaOH($cm^3$) | % Hydrolysis | Vol NaOH($cm^3$) | % Hydrolysis |
| 0 | 1.05 | 0 | 1.00 | 0 |
| 1 | 6.75 | 37.0 | 0 | 0 |
| 2 | 12.70 | 69.7 | 0 | 0 |
| 3 | 18.10 | 99.3 | 0 | 0 |

From this it is apparent that the allyl ether linkage is much more chemically stable than the acrylate linkage.

EXAMPLE 5

In order to demonstrate the usefulness of polymers of this type for thickening aqueous alkaline solution e.g. caustics and paint removers, solutions of POLYMER A and POLYMER F were prepared 2.0% active in 10% NaOH solution. The resulting solution viscosities were measured using a Brookfield RVT viscometer over a range of speeds.

TABLE 5

| PRODUCT | BROOKFIELD VISCOSITY (cp) | | | |
|---|---|---|---|---|
| | 2.5 rpm | 10 rpm | 20 rpm | 100 rpm |
| POLYMER A | 52000 | 24500 | 16000 | 4600 |
| POLYMER F | 54000 | 16500 | 9000 | 2500 |

This clearly demonstrates the high level of thickening efficiency which polymers of this type are able to exhibit in such systems.

EXAMPLE 6

Emulsion Paints

Two matt emulsion paints (MEP No.1 and 2) were prepared using polymers according to the invention and one (MEP No.3) using a conventional paint thickener Natrosol 250 HR*. Each paint was made to 65% pigment volume concentration from the following "Mill Base" and "Let Down" recipes.

| Mill Base | Parts by weight |
|---|---|
| Water | $15.00^1$/$19.30^2$ |
| Dispersing agent | 0.46 |
| Bactericide | 0.05 |
| Hexylene glycol | 1.00 |
| Defoamer | 0.05 |
| Thickener | $1.00^1$/$0.30^2$ |
| 0.880 ammonia | 0.20 |
| Titanium dioxide | 19.75 |
| Calcium carbonate | 19.75 |
| Talc | 6.59 |
| Let Down | |
| Latex binder | 16.18 |
| Coalescing solvent | 0.80 |
| Water | $18.77^1$/$15.37^2$ |
| 0.880 ammonia | 0.40 |

[1]Quantity used with aqueous thickener of the invention in paints MEP1 and 2.
[2]Quantity used with conventional thickener in paint MEP3.
*Natrosol is a trade mark.

The components of the "Mill Base" were milled under high shear at 2290 rpm to Hegman Gauge 7–8. The components of the "Let Down" were then added at a reduced speed of 890 rpm. The paints were then stored for a period of 7 days at room temperature before characterization.

TABLE 6

| Paint Sample Code | Thickener (0.3% dry on total) | Final pH | Brookfield RVT @ 20 rpm (Poise) | Stormer Viscosity (Krebs Units) | ICI Rotothinner Viscosity (Poise) |
|---|---|---|---|---|---|
| MEP-1 | POLYMER A | 9.0 | 120 | 108 | 9.5 |
| MEP-2 | POLYMER W | 9.0 | 252 | 121 | 10.0 |
| MEP-3 | NATROSOL 250 HR | 9.1 | 120 | 105 | 7.6 |

Each of the above points was evaluated for its spatter properties using the following test procedure.

A board, approximately 30×42 cm was mounted vertically above a work bench the bottom edge being positioned 20 cm above the surface of the bench. A piece of black card measuring 24×31.5 cm was then placed on the surface of the bench top directly below the board in order to catch any droplets or "paint mist" spattering from the roller.

Each paint was poured in turn into a roller tray and applied to the vertical board using a lambswool roller. The standard conditions adopted for this test involved 10 upstrokes and downstrokes of the roller on the board. The black card was then removed for inspection. The degree of spatter was assessed visually and rated on a scale of 1-5 with 1 being excellent; i.e. no spatter and 5 being very poor; i.e. severe spatter. The results recorded were as follows:

| Paint Sample Code | Spatter |
| --- | --- |
| MEP-1 | 2 - Very Good |
| MEP-2 | 1 - Excellent |
| Mep-3 | 4 Poor |
| Example 7 | |

EXAMPLE 7

Carpet backing formulations

The use of products of this type as thickeners for carpet backing formulations has been demonstrated according to the following information.

| Formulation | A | B |
| --- | --- | --- |
| Total Solids (nominal) | 76% | 40% |
| Filler: Binder Ratio (dry:dry) | 8:1 | 1:2 |
| Latex Binder (50% active) | 15.6 | 49.5 |
| Calcium carbonate filler | 67.5 | 13.0 |
| Surfactant | 0.1 | 0.1 |
| Dispersant | 1.0 | 1.0 |
| Thickener + Water | to 100 | to 100 |

The amount of thickener was selected such that Formulation A had viscosity 9000 cp and B had viscosity 6000 cp, Brookfield RVT viscometer, spindle 5 at 10 rpm.

In this instance Polymer E fully neutralized as Na+ salt was compared as thickeners with VISCALEX AH 10 (carboxylated acrylic gel polymer sold by Allied Colloids Limited as a thickener for carpet backing compounds). The following results were obtained.

TABLE 7

| | BROOKFIELD VISCOSITY (CP) | | | |
| --- | --- | --- | --- | --- |
| | FORMULATION A | | FORMULATION B | |
| THICKENER TYPE | Viscalex AH10 | Polymer E | Viscalex AH10 | Polymer E |
| ADDITION LEVEL (% Dry on Total) | 0.16 | 0.035 | 0.90 | 0.15 |
| Initial Viscosity | 9100 | 8600 | 5800 | 6000 |
| Day 1 Viscosity | 9000 | 8600 | 5600 | 6200 |
| Day 2 Viscosity | 9000 | 8600 | 5800 | 6200 |

The improved level of efficiency of the polymers of the invention is clearly demonstrated.

Printing Pastes

In the examples which follow, all print paste viscosities were measured with a Brookfield RVT viscometer at speed 10 rpm, spindle 6° at 20° C. Printing was carried out using a variety of screens, each being constructed of 156 mesh polyester filament.

EXAMPLE 8

A printing clear was prepared according to the recipe given in Table 8.

TABLE 8

| COMPONENT | % by wt |
| --- | --- |
| Ammonia (0.880) | 0.5 |
| Emulsifier* | 2.0 |
| Odourless kerosene | 40.0 |
| Binder latex (40% solids) | 12.0 |
| Polymer W | 1.7 |
| Water | 43.8 |

*e.g., ethoxylated nonyl phenol (14 moles ethylene oxide)

A viscosity of 20,000 cp was obtained after stirring for 10 minutes. The clear was then divided and pigment printing pastes prepared by mixing 9.6 parts of this stock with each of the following pigments:
(i) Imperom Blue KRR - 4 parts
(ii) Helizarin Bordeaux R - 4 parts These pastes were then re-thickened by stirring in additional quantities of Polymer W until a viscosity of 20,000 cp was again obtained. The amounts of Polymer W required were found to be 0.19 parts and 0.23 parts for the blue and bordeaux pigments respectively.

Both pastes were printed on to a plain woven 50/50 cotton fabric. The prints were then dried and cured for 4.5 minutes of 150° C. In each case excellent colour yield, brightness and find line definition were observed.

EXAMPLE 9

A series of printing clears was prepared in which the concentration of Polymer A was progressively increased. The recipes are given in Table 9a below, where all figures refer to parts by weight:

TABLE 9a

| | Paste | | | |
| --- | --- | --- | --- | --- |
| Component | A | B | C | D |
| Ammonia (0.880) | 0.5 | 0.5 | 0.5 | 0.5 |
| Binder latex (40% solids) | 12.0 | 12.0 | 12.0 | 12.0 |
| Water | 85.88 | 85.65 | 85.56 | 85.21 |
| Thickener+ | 1.62 | 1.60 | 1.44 | 1.29 |
| Polymer A | — | 0.25 | 0.50 | 1.00 |

+The thickener used was a 50% active dispersion of a cross-linked polyacrylic acid such on described in US 4554018. In each case the concentration employed was chosen so as to give a viscosity of 20,000 cp.

Printing pastes were then prepared from each clear by mixing 96 parts with 4 parts of the following black pigments and stirring by efficient mechanical means for 5 minutes.
(i) Imperon Black KGF
(ii) Acramin Black FBRK The viscosity of each paste was then remeasured at 20° C. The results were as follows:

TABLE 9b

| PASTE | VISCOSITY (cp) Black KGF | Black FBRK |
|---|---|---|
| A | 50,000 | 66,000 |
| B | 29,400 | 30,600 |
| C | 23,000 | 25,200 |
| D | 19,600 | 20,200 |

The two pastes A, prepared without the addition of Polymer A, were highly viscous gels and were considered unsuitable for practical use. As the concentration of Polymer A was increased, the increase in viscosity, compared with the initial clears, was greatly reduced. All pastes B, C and D were of the correct rheology for commercial printing.

EXAMPLE 10

Printing pastes were prepared using Polymer A and a cross-linked polyacrylic acid thickener in an analagous manner to that outlined above. The recipes were as follows, all figures referring to parts by weight.

TABLE 10a

| Component | A | B | C | D | E | F | G | H |
|---|---|---|---|---|---|---|---|---|
| Ammonia (0.880) | 0.5 | 0.5 | 0.5 | 0.5 | 0.5 | 0.5 | 0.5 | 0.5 |
| Binder latex (40%) | 12.0 | 12.0 | 12.0 | 12.0 | 12.0 | 12.0 | 12.0 | 12.0 |
| Water | | | | to 100% | | | | |
| Thickener | 1.62 | 1.61 | 1.44 | 1.29 | 1.65 | 1.84 | 1.82 | 1.79 |
| Polymer A | — | 0.25 | 0.5 | 1.0 | — | 0.25 | 0.5 | 1.0 |
| Imperon Blue KRR | 4.0 | 4.0 | 4.0 | 4.0 | — | — | — | — |
| Helizarin Bordeaux R | — | — | — | — | 4.0 | 4.0 | 4.0 | 4.0 |

Each paste was printed on to a substrate which was known to cause severe flushing or haloing when printed with many existing formulations. The fabric chosen was a plain woven 50/50 polyester/cotton which had been preresinated using a DHDHEU resin and also contained a magnesium chloride catalyst.

The severity of flushing was critically assessed by using a printing screen which consisted of a series of five lines and criss-cross patterns. Immediately after printing, the fabric was allowed to dry for 2 minutes under atmospheric conditions before being dried at 150° C. for 2 minutes (drying quickly causes the movement of print paste to be halted).

The extent to which flushing occurred was then assessed on an arbitrary 1–10 scale, where 1 indicates a perfect print without any sign of flushing and 10 indicates severe flushing. The results are given below:

TABLE 10b

| PRINT PASTE | BLUE | PASTE | BORDEAUX |
|---|---|---|---|
| A | 8 | E | 8 |
| B | 5 | F | 3 |
| C | 3 | G | 3 |
| D | 2 | H | 2 |

The inclusion of Polymer A into the printing paste is clearly seen to bring about a dramatic improvement in print quality, with a 1% addition virtually eliminating flushing. It is considered that a rating of 3 or below would represent a commercially acceptable print.

EXAMPLE 11

A latex was formed by oil in water emulsion polymerization using ammonium persulphate of 40 parts by methacrylic acid, 50 parts by weight ethyl acrylate and 10 parts by weight of a surfactant ether formed from allyl chloride and the reaction product of polyoxyethylene (10 moles) stearyl ether with sodium methoxide.

200 grams of the latex was homogenised into an oil phase comprising 7.0 grams of Span 80, 23.3 grams of a 30% active solution of a 2:1 molar copolymer of cetostearyl methacrylate:hydroxyethylmethacrylate in SBP11, 39.2 grams of Pale Oil 60 and 96.0 grams of SBP11. The resulting inverse emulsion was then dehydrated by distilling off water and SBP11 under reduced pressure to a final pressure of 10 mm.Hg and a temperature of 95° C.

The resulting anhydrous polymer-in-oil dispersion was activated by mixing in 5.6 grams of Ethylan D254 to produce a self-emulsifiable liquid polymer-in-oil dispersion having 50% active solids. Span and Ethylan are trade marks.

Upon addition of this dry dispersion to deionised water or 0.5% NaCl solution to form a 2% solution, the Brookfield viscosity at spindle 6 is 352,000 or 480,000 cps respectively at 2.5 rpm and 28,000 or 35,000 cps at 100 rpm.

EXAMPLE 12

The process of Example 1, for Polymer A, was repeated except that the free acid monomer was replaced by a free base monomer as indicated in Table 12a. The Perlankrol surfactant was replaced by Ethylan HA (non-ionic).

Polymers having the compositions indicated in the table below were prepared at 1% active in water by neutralisation with HCl, and the resulting viscosity was measured using a Brookfield RVT viscometer.

TABLE 12a

| Product | Monomer Ratio (% by wt.) DMAEMA | NMA | AES | Surfactant Composition n | R | Solution Viscosity (cP) @ 10 rpm |
|---|---|---|---|---|---|---|
| Polymer AH | 45 | 35 | 20 | 10 | stearyl | 29000 |
| Polymer AJ | 50 | 30 | 20 | 10 | stearyl | 68000 |
| Polymer AK | 55 | 25 | 20 | 10 | stearyl | 136000 |
| Polymer AL | 60 | 20 | 20 | 10 | stearyl | 80000 |
| Polymer AM | 40 | 35 | 25 | 10 | stearyl | 74000 |
| Polymer AN | 40 | 30 | 30 | 10 | stearyl | 27000 |

TABLE 12a-continued

| Product | Monomer Ratio (% by wt.) | | | Surfactant Composition | | Solution Viscosity (cP) @ 10 rpm |
|---|---|---|---|---|---|---|
| | DMAEMA | NMA | AES | n | R | |
| Polymer AP | 40 | 25 | 35 | 10 | stearyl | 5200 |
| Polymer AQ | 40 | 20 | 40 | 10 | stearyl | 1700 |

DMAEMA = dimethylaminoethylmethacrylate
MMA = methylmethacrylate
AES = allyl ether surfactant In order to demonstrate the effectiveness of polymers of this type in thickening highly acidic media Polymer AH was used to thicken 15% solutions of different acids at 5% active polymer. The results obtained are given in Table 12B.

TABLE 12b

| Product | Acid Type (solution conc$^3$ w/w) | Solution Viscosity (cP) @ 10 rpm |
|---|---|---|
| Polymer AH | 15% hydrochloric acid | 2,200 |
| Polymer AH | 15% phosphoric acid | 6,400 |
| Polymer AH | 15% acetic acid | 9,600 |

This polymer is useful for thickening aqueous acidic liquors, such as battery liquids.

EXAMPLE 13

181.8 parts of a 79.2% solution of acrylic acid in water, 0.4 parts of Tetralon B, 5.8 parts of the allyl ether of a 10 mole ethoxylate of stearyl alcohol, 118 parts of water, 0.0424 parts of AZDN and 116 parts of a 29.9% solution of ammonia in water were mixed to form an aqueous solution. A non-aqueous liquid phase was formed from 7.4 parts of Span 80, 42.4 parts of a 30% solution in SBP11 of an inverse dispersion stabiliser (copolymer of 2 moles cetostearyl methacrylate with 1 mole of methacrylic acid), 127.3 parts of Pale Oil 60 and 145.7 parts of SBP11.

The aqueous phase was homogenised into the oil phase, deoxygenated and polymerised using 0.042 parts of sodium metabisulphite dissolved in 2.058 parts of water and tertiary butyl hydroperoxide added continuously as a 0.5% solution in water at a rate of 0.14 parts per minute.

The resulting inverse dispersion of hydrated polymer was distilled to yield a dehydrated concentrated polymer dispersion to which was added 2 parts of a 5 mole ethoxylate of nonyl phenol and 1 part of a 4 mole ethoxylate of a broad cut lauryl alcohol per 100 parts of concentrated dehydrated dispersion.

This formed a dispersion of 50% active copolymer which dispersed with agitation in water to yield a highly viscous polymer solution with the characteristic 'soap gel' rheology of associated water soluble polymers. This process was repeated except that the aqueous phase contained in addition 0.063 parts of methylene bis acrylamide as bi-functional crosslinking comonomer. The resultant dehydrated polymer particles swelled in water to form a highly viscous but non-viscoelastic paste useful as a vehicle for printing textiles and other articles particularly on cloth containing residual electrolyte where pastes thickened with conventional polyammonium acrylate microgel latices give holoing, bleading or flushing of print colour.

Polymers produced by this method but omitting the cross-linking monomer may be made and may be as exemplified in EP No.-A-0172724.

EXAMPLE 14

A range of polymers were made by gel polymerisation using differing amounts of acrylamide, sodium acrylate, allyl ether and cross linking agent, and by using different allyl ethers. The product of the polymerisation was then dried and comminuted to give particles having sizes in the range 200 to 500 microns.

0.5 g of each polymer was added to 400 cc of a swelling solution that was deionised water or aqueous sodium chloride of various concentrations. The samples were allowed to equilibrate for 30 minutes and the swollen gel particles were then separated from the medium by filtration through a nylon filter mesh and weighed to give an indication of absorbency. The values are expressed in percentage based on the amount of deionised water that was absorbed by each polymer. The monomer feed and the results are shown in the following table. In this table R is the hydrophobic group and n is the number of ethylene oxide groups between it and the allyl ether linkage.

| Polymer | 1 | 2 | 3 | 4 | 5 | 6 | 7 | 8 |
|---|---|---|---|---|---|---|---|---|
| Acrylamide | 60 | 50 | 45 | 45 | 50 | 50 | 50 | 50 |
| Sodium Acrylate | 40 | 40 | 40 | 40 | 40 | 40 | 40 | 40 |
| Methylene bis acrylamide | 0.03 | 0.06 | 0.06 | 0.06 | 0.03 | 0.06 | 0.03 | 0.06 |
| Allyl ether | 0 | 10 | 15 | 15 | 10 | 10 | 10 | 10 |
| R | — | $C_{18}H_{37}$ | $C_{18}H_{37}$ | $C_{18}H_{37}$ | $C_{12}H_{25}$ | $C_{12}H_{25}$ | $C_{18}H_{37}$ | $C_{18}H_{37}$ |
| n | — | 10 | 10 | 20 | 23 | 23 | 20 | 20 |
| Deionised water | 100 | 100 | 100 | 100 | 100 | 100 | 100 | 100 |
| 0.1% NaCl | 21.7 | 32.4 | 25.5 | 33.8 | 27.3 | 21.8 | 25.1 | 34.0 |
| 0.25% NaCl | 12.5 | 22.4 | 16.7 | 22.9 | 18.8 | 14.9 | 16.6 | 23.8 |
| 0.5% NaCl | 10.3 | 16.5 | 11.6 | 14.9 | 15.1 | 11.6 | 11.9 | 17.4 |
| 1% NaCl | 7.9 | 8.8 | 10.0 | 11.2 | 11.6 | 7.9 | 9.8 | 13.6 |

Comparison of polymers 3 and 4 shows the advantage that follows from increasing the length of the ethoxy chain. Very poor results are obtained when there is no ethoxy chain, as in U.S. Pat. No. 4,190,562.

Linear water-soluble polymers may be made as in this example but omitting the cross-linking monomer. Thus they may be as exemplified in EP No.-A-0172723.

The entire disclosure of Ser. Nos. 766,097 and 766,098 filed Aug. 15, 1985 is hereby incorporated by reference.

We claim:

1. A polymer that is substantially non swelling and insoluble in water but soluble or swellable in aqueous acid or alkali, and formed by oil in water emulsion polymerisation of a polymerisable mixture formed by mixing monomers consisting essentially of
   (a) 5 to 90% by weight of monolthylenically unsaturated ionic monomer
   (b) 5 to 90% by weight of monoethylenically unsaturated substantially non-ionic monomer
   (c) 0.5 to 90% by weight of a monoethylenically unsaturated monomer that carries a pendant group $-B_nR$ where B is ethylenoxy, n is zero or a positive integer and R is a hydrophobic hydrocarbyl group of at least 8 carbon atoms
   (d) 0 to 0.2% by weight of cross linking monomer, and in which monomer (c) is an allyl ether of the formula $CH_2=CR'CH_2O_nR$ where R' is hydrogen or methyl and in which B, n and R are as defined above and monomer (d) consists essentially of polyethylenically unsaturated monomer.

2. A polymer according to claim 1 formed from 20 to 60% by weight (meth) acrylic acid, 2 to 50% by weight alkyl (meth) acrylate where alkyl is methyl, ethyl or butyl, 2 to 50% by weight of the allyl ether and 0 to 0.2% of the said cross linking monomer.

3. A polymer according to claim 1 in which monomer (a) is selected from the group consisting of acrylic acid and methacrylic acid.

4. A polymer according to claim 1 in which monomer (a) comprises a vinyl tertiary amine monomer.

5. A polymer according to claim 1 in which monomer (a) comprises a dialkylaminoalkyl (meth) acrylate monomer or a dialkylaminoalkyl (meth) acrylamide monomer.

6. A polymer according to claim 1 in which monomer (b) is selected from styrene, alkyl-substituted styrenes, halo-substituted styrenes, (meth) acrylonitrile, vinyl alkanoates, vinyl halides, vinylidene halides, hydroxy alkyl (meth) acrylates, alkoxy alkyl (meth) acrylates and alkyl (meth) acrylates.

7. A polymer according to claim 1 in which, in monomer (c), n is from 2 to 100.

8. A polymer according to claim 1 in which, in monomer (c), R is a hydrophobic hydrocarbyl group of 8 to 30 carbon atoms selected from alkyl, aralkyl, aryl, alkaryl and cycloalkyl and R' is hydrogen.

9. A polymer according to claim 1 in which, in monomer (c), R contains 10 to 24 carbon atoms and is selected from alkyl and alkaryl and n is an integer of from 5 to 100.

10. A composition comprising a polymer according to claim 1 which is in the form of an aqueous emulsion at a pH such that the polymer is insoluble and substantially unswollen and non-thickening but can be converted to a dissolved or swollen and thickening state by the addition of acid or alkali.

11. An aqueous composition that has been thickened by adding to the composition a thickening amount of a polymer according to claim 1 and, before or after the addition, adjusting the pH such that the polymer is dissolved or swollen.

12. A composition according to claim 11 selected from print pastes and emulation paints.

13. A composition according to claim 12 and which also contains surfactant in an amount of 0.05 to 1 part per part by weight polymer.

14. A linear polymer having intrinsic viscosity of at least 0.5 (measured as single point at 0.05% concentration in methanol) and formed by polymerisation in the absence of a cross-linking agent of
   (a) 0 to 90% by weight of monoethylenically unsaturated ionic monomer
   (b) 0 to 90% by weight of monoethylenically unsaturated substantially non-ionic monomer
   (c) 0.5 to 100% by weight of a monoethylenically unsaturated monomer that carries a pendant group $-B_nR$ where B is ethylenoxy, n is zero or a positive integer, and R is a hydrophobic hydrocarbyl group of at least 8 carbon atoms
   and in which monomer (c) is an allyl ether of the formula $CH_2=CR'CH_2OB_nR$ where R' is hydrogen or methyl and B, n and R are as defined above.

15. A linear, water soluble, polymer having intrinsic viscosity at least 0.5 (measured as single point at 0.05% concentration in methanol) and formed by polymerisation in the absence of a cross-linking agent of
   (a) 0 to 90% by weight of monoethylenically unsaturated ionic monomer
   (b) 0 to 90% by weight of monoethylenically unsaturated substantially non-ionic monomer
   (c) 0.5 to 100% by weight of a monoethylenically unsaturated monomer that carries a pendant group $-B_nR$ where B is ethylenoxy, n is zero or a positive integer, and R' is a hydrophobic hydrocarbyl group of at least 8 carbon atoms
   and in which monomer (c) is an allyl ether of the formula $CH_2=CR'CH_2OB_nR$ where R is hydrogen or methyl and B, n and R are as defined above and in which monomers (a) and (b) are water soluble and the polymer is formed from 2 to 15% by weight of the allyl ether and from 5 to 98% by weight of the monomers (a) and (b), and the polymer has molecular weight above 0.5 million.

16. A polymer according to claim 15 in which monomer (a) is selected from the group consisting of acrylic acid and methacrylic acid.

17. A polymer according to claim 15 in which monomer (a) comprises a vinyl tertiary amine monomer.

18. A polymer according to claim 15 in which monomer (a) comprises a dialkylaminoalkyl (meth) acrylate monomer or a dialkylaminoalkyl (meth) acrylamide monomer.

19. A polymer according to claim 15 formed from 5 to 50% by weight monoethylenically unsaturated carboxylic acid or sulphonic acid monomer, 50 to 90% by weight acrylamide and 2 and 30% by weight of the allyl ether.

20. A polymer according to claim 15 in which, in monomer (c), n is from 2 to 100.

21. A polymer according to claim 15 in which, in monomer (c), R is a hydrophobic hydrocarbyl group of 8 to 30 carbon atoms selected from alkyl, aralkyl, aryl, alkaryl and cycloalkyl and R' is hydrogen.

22. A polymer according to claim 15 in which, in monomer (c), R contains 10 to 24 carbon atoms and is selected from alkyl and alkaryl and n is an integer of from 5 to 100.

23. An aqueous composition thickened by the presence therein of a thickening amount of a polymer according to claim 15.

24. A cross linked polymer formed by polymerisation of a polymerisable mixture formed by mixing monomers consisting essentially of
   (a) 0 to 90% by weight of monoethylenically unsaturated ionic monomer
   (b) 0 to 90% by weight of monoethylenically unsaturated substantially non-ionic monomer
   (c) 0.5 to 100% by weight of a monoethylenically unsaturated monomer that carries a pendant group $-B_nR$ where B is ethylenoxy, n is zero or a positive integer, and R is a hydrophobic hydrocarbyl group of at least 8 carbon atoms
   (d) 0.0005 to 0.2% by weight of cross linking monomer,
   and in which monomer (c) is an allyl ether of the formula $CH_2=CR'CH_2B_nR$ where R' is hydrogen or methyl and B, n and R are as defined above and monomer (d) consists essentially of polyethylenically unsaturated monomer.

25. A cross linked, water swellable, polymer formed by polymerisation of a polymerisable mixture formed by mixing monomers consisting essentially of
   (a) 0 to 90% by weight of monoethylenically unsaturated ionic monomer
   (b) 0 to 90% by weight of monoethylenically unsaturated substantially non-ionic monomer
   (c) 0.5 to 100% by weight of a monoethylenically unsaturated monomer that carries a pendant group $-B_nR$ where B is ethylenoxy, n is zero or a positive integer, and R is a hydrophobic hydrocarbyl group of at least 8 carbon atoms
   (d) 0.0005 to 0.2% by weight of cross linking monomer,
   and in which monomer (c) is an allyl ether of the formula $CH_2=CR'CH_2B_nR$ where R' is hydrogen or methyl and B, n and R are as defined above, monomer (d) consists essentially of polyethylenically unsaturated monomer, monomers (a) and (b) are water soluble and the polymer is formed from 2 to 95% by weight of the allyl ether and 5 to 98% by weight of the monomers (a) and (b).

26. A polymer according to claim 25 in which monomer (a) is selected from the group consisting of acrylic acid and methacrylic acid.

27. A polymer according to claim 25 in which monomer (a) comprises a vinyl tertiary amine monomer.

28. A polymer according to claim 25 in which monomer (a) comprises a dialkylaminoalkyl (meth) acrylate monomer or a dialkylaminoalkyl (meth) acrylamide monomer.

29. A polymer according to claim 25 in which, in monomer (c), n is from 2 to 100.

30. A polymer according to claim 25 in which monomer (a) is acrylic acid and monomer (b) is acrylamide.

31. A polymer according to claim 25 in which, in monomer (c), R is a hydrophobic hydrocarbyl group of 8 to 30 carbon atoms selected from alkyl, aralkyl, aryl, alkaryl and cycloalkyl and R' is hydrogen.

32. A polymer according to claim 25 in which, in monomer (c), R contains 10 to 24 carbon atoms and is selected from alkyl and alkaryl and n is an integer of from 5 to 100.

33. A polymer according to claim 25 in the form of particles having a size of below 4 m and dispersed in a non-aqueous liquid.

34. An aqueous composition thickened by the presence therein of a thickening amount of a polymer according to claim 33.

35. A polymer according to claim 25 in the form of absorbent particles having a size of from 50 m to 500 m, and in which the ionic monomer (a) is anionic.

36. A polymer according to claim 1 in which the polymerisable mixture is free of cross linking monomer.

37. A polymer according to claim 1 in which the amount of cross linking monomer is 0.0005 to 0.2%.

* * * * *